United States Patent [19]
Krell et al.

[11] Patent Number: 6,066,584
[45] Date of Patent: May 23, 2000

[54] SINTERED $AL_2O_3$ MATERIAL, PROCESS FOR ITS PRODUCTION AND USE OF THE MATERIAL

[75] Inventors: Andreas Krell; Paul Blank, both of Dresden, Germany

[73] Assignee: Fraunhofer-Gesellschaft zur Förderung der Angewandten Forschung e.V., Germany

[21] Appl. No.: 08/727,409

[22] PCT Filed: Apr. 19, 1995

[86] PCT No.: PCT/EP95/01474

§ 371 Date: Jan. 31, 1997

§ 102(e) Date: Jan. 31, 1997

[87] PCT Pub. No.: WO95/28364

PCT Pub. Date: Oct. 26, 1995

[30] Foreign Application Priority Data

Apr. 19, 1994 [EP] European Pat. Off. .............. 94106040

[51] Int. Cl.⁷ .................................................. C04B 35/10
[52] U.S. Cl. ......................... 501/127; 501/128; 501/132; 501/153; 264/653; 264/603; 264/645
[58] Field of Search ..................... 501/127, 153, 501/128, 132; 51/307, 309; 264/621, 653, 603, 645

[56] References Cited

U.S. PATENT DOCUMENTS

| | | | |
|---|---|---|---|
| 4,052,538 | 10/1977 | Eddy et al. | 264/56 |
| 4,952,537 | 8/1990 | Hayashi et al. | 501/153 |
| 5,114,891 | 5/1992 | Kunz et al. | 501/127 |
| 5,215,551 | 6/1993 | Hatanaka et al. | 501/153 |
| 5,261,930 | 11/1993 | Fliedner et al. | 51/309 |
| 5,547,479 | 8/1996 | Cornwell et al. | 501/153 |
| 5,645,618 | 7/1997 | Monroe et al. | 501/153 |

*Primary Examiner*—Michael Marcheschi
*Attorney, Agent, or Firm*—Medlen & Carroll, LLP

[57] ABSTRACT

The invention relates to the field of ceramics and concerns sintered $Al_2O_3$ compositions produced from corundum powder and also methods for the use of the invented compositions as medical implants or tool material. To produce such materials, an initially unsintered precursor having a relative density of $\rho \geqq 55\%$ is produced from $\alpha$-$Al_2O_3$ powder having defined properties using at least two different dispersing methods, this precursor is subsequently subjected to heat treatment and sintering.

53 Claims, No Drawings

SINTERED AL$_2$O$_3$ MATERIAL, PROCESS FOR ITS PRODUCTION AND USE OF THE MATERIAL

The invention relates to the field of ceramics and concerns sintered Al$_2$O$_3$ materials and processes for their production. The sintered materials can be used as medical implants, as wear products, as cutting tools or as abrasives.

The intensive efforts of recent years aimed at producing monolithic sintered Al$_2$O$_3$ products having grain sizes of less than 2 μm and improved mechanical properties from corundum powder followed essentially two routes:

use of very fine submicron or nanosize powders, addition of substances to lower the temperature required for sintering to full density.

Although the very fine starting materials have the desired high sintering activity, owing to their poor densification behaviour they at the same time bring with them considerable problems in shaping. The low-cost uniaxial dry pressing process, which has hitherto been predominantly employed, leads to insufficient green density or to density inhomogeneities in the shaped body and, on sintering, defects which reduce the hardness and strength. For these reasons, other shaping processes such as cold isostatic pressing, extrusion, pressure or centrifugal casting or gel casting are employed.

An Al$_2$O$_3$ grain size in the sintered body of 0.8 μm and a hardness of HV20=1920 have been achieved by extrusion of ceramic compositions comprising submicron powders and sintering at 1400° C. (G. Riedel, et al., Silicates Industriels (1989) 1/2,29–35). The powder used here had a mean particle size of 0.45 μm and a d$_{84}$ value, which describes the width of the coarse particle fraction of the particle size distribution, of 1.0 μm.

In the case of very fine Al$_2$O$_3$ powders having d$_{50}$<0.4 μm and a d$_{84}$ value, which describes the width of the coarse particle fraction of the particle size distribution, of <0.7 μm, slip casting has also been successfully used recently (T.-Sh. Yeh et al., J. Am. Ceram. Soc. (1988), pp. 841–844), also in combination with the application of pressure (pressure filtration: F. F. Lange et al., Bull. Am. Ceram. Soc. (1987), pp. 1498–1504; Vacuum Pressure Filtration: H. Mizuta et al., J. Am. Ceram. Soc. (1992), pp. 469–473). As shown, for example, by Mizuta et al., these complicated processes enable the best mechanical properties up to now for pure sintered corundum to be achieved, but according to this prior art no Vickers low-load hardnesses of ≧2000 or flexural strengths of ≧800 MPa were measured even when hot isostatic pressing (HIPping) was employed.

The usefulness of pressureless casting processes such as gel casting or enzyme-controlled coagulation for producing pure Al$_2$O$_3$ ceramics has hitherto been restricted to corundum powders having mean particle sizes of more than 0.4 μm (A. C. Young, et al., J. Am. Ceram. Soc. (1991)3, 612–618), so that the mean grain sizes of the dense sintered microstructures produced were always greater than 1.5 μm. In the example cited, the strengths achieved remained below 300 MPa.

The opportunities for improving the mechanical properties and the grain fineness of sintered Al$_2$O$_3$ products produced from corundum powder by addition of substances which promote sintering are very limited. The temperature required for sintering submicron Al$_2$O$_3$ powders to full density is, in particular, reduced to 1200° and less by addition of more than 1% of dopants which form liquid phases during sintering, but the strengths remain at the level usual for traditional sintered corundum, viz. about 400 MPa (L. A. Xue et al., J. Am. Ceram. Soc., (1991), pp. 2011–2013), and the widespread formation of grain boundary phases brings with it unfavourable high-temperature properties.

Although the relationship between defect structure and strength of brittle solids has been well known for a long time, most studies are restricted to the purely qualitative determination of relevant defect types; even a characterization of only relative defect size distributions (H. E. Exner et al., Mater. Sci. Eng. 16 (1974), pp. 231–238) is rare. As regards the technology dependence of the actually important absolute defect frequency per volume or analysed area, as studied, for example, for glass (J. R. Matthews et al., J. Am. Ceram. Soc. 59 (1976), pp. 304–308), nothing is known for Al$_2$O$_3$ ceramics. There are absolutely no prior studies on the effect of such defects on the Vickers hardness.

In evaluating the hardness of Al$_2$O$_3$ ceramics thus produced, the influence of the test loading used for the indenter first has to be taken into account. The Vickers hardness of Al$_2$O$_3$ is, for a single-crystal as well as polycrystalline material, dependent on the load in a complex way (A. Krell, Kristall und Technik (1980) 12,1467–74). The following material behaviour is typical:

relatively little load influence at a relatively high test load ≧50 N, decreasing loading first produces increasing hardness values, when the test load is reduced further to from <1 to 5 N, the hardness can fall again.

Similar behaviour is found for the Knoop hardness, although there are certain systematic differences between the numerical results by the Knoop and Vickers methods.

According to the prior art described below for the sintered Al$_2$O$_3$ products produced by means of known processes from corundum powder, the long-established recognition that, independently of the respective test load, a grain size reduction in the range 2–0.2 μm cannot make possible a hardness increase beyond the known upper limits of HV10≈2000 (low-load hardness) or HV0.2≈ 2500 (microhardness) applies (S. D. Skrovanek et al., J. Am. Ceram. Soc. (1979)3/4, 215–216). For the above reasons, a comparison of hardness data in the literature is only informative when the load dependence of the hardness has been examined and the associated test conditions are indicated. This is particularly true because the influence of the test load varies greatly even within a material group, for example sintered corundum, as a function of additives, residual porosity and, in particular, the state of the surface. Owing to the wide variety of data in the prior art, for which specific details are rarely given, the data for the particle size influence on the microhardness and low-load hardness or macrohardness fluctuate within wide limits.

Microhardness HV (in the range HV0.1–HV0.5, i.e. in the range of the possible maximum of the hardness-load curve)

for single crystals: 2300–2700 (A. G. Evans et al., J. Am. Ceram. Soc. (1976)7/8, 371–372)

for sintered corundum with D≈2 μm at relative density ρ≧99%; 2000–2600 (S. D. Skrovanek et al., J. Am. Ceram. Soc. (1979)3/4,215–216

Vickers low-load hardness and macrohardness (test load ≧10 N)

for single crystals: 1400–1700 (A. Krell, Kristall und Technik (1980)12,1467–1476)

for sintered corundum with D≈2 μm at relative density ρ≧99%: 1650–1850 (A. Krell, Kristall und Technik (1980)12,1467–1476)

for sintered corundum products with D≈0.45 μm, produced by powder technology, at relative density ρ≈98–98.5%: 1900–2000 (G. Riedel et al., Silicates Industriels (1989)1/2, 29–35).

Specific studies by Skrovanek et al. on the dependence of hardness on grain size in virtually fully densified hot-pressed sintered corundums having a gradated reduction in grain size showed a hardness increase proportional to $D^{-1/2}$ only down to the range 3–4 μm. According to general opinion, this is caused by the increasing hindrance of the displacement motion in the smaller grains. However, further grain size reductions down to 1.7 μm gave no further increase in the hardness; the hardness remained constant in this range of small grain sizes. This finding has hitherto never been contradicted because, according to general opinion a further increase in hindrance of the displacement motion with decreasing grain size, and therefore increasing hardness, can no longer be expected when the grain sizes are of the size range of the displacements. Since typical sizes of displacements (displacement loops) observed in corundum by means of transmission electron microscopy are in the micron range, the reduction in the grain size effect on the hardness at grain sizes of less than 3–4 μm was so self-evident that this question was not examined in more detail.

The disadvantage of the sintered $Al_2O_3$ products known from the prior art and produced from corundum powder is that no sintered $Al_2O_3$ products having a very low level of defect and very high hardness or high hardness and strength are known and able to be produced. Without conclusive solutions of the problems having become known up to now, current developments are being concentrated internationally on two directions which are regarded as promising (T. J. Carbone, p. 107 in: L. D. Hart (Editor), "Alumina Chemicals Science and Technology Handbook", The Am. Ceram. Soc., Westerville, Ohio, 1990):

(1) improvement of the sol/gel technologies with additions of nuclei (e.g. G. L. Messing and M. Kumagai in Bull. Am. Ceram. Soc. 73(1994)88–91), (2) the development and use of powders extremely uniform particle size believed to be ideal ("monosized", "uniform-sized") as described by K. Yamada in "Alumina Chemicals Science and Technology Handbook" (Editor L. D.

Hart, The Am. Ceram. Soc., Westerville, Ohio, 1990, page 564)

It is an object of the invention to provide sintered $Al_2O_3$ materials having improved mechanical properties, in particular having high hardness and/or strength.

The sintered $Al_2O_3$ materials of the invention having an $Al_2O_3$ content of from 95 to 100% by volume and a Vickers low-load hardness of $\geq 2000$ at a test load of from 10 N to 100 N (HV1 to HV10) have a relative sintered density of $\rho \geq 98.5\%$, microstructures having mean grain sizes of $\leq 1.5$ μm and a frequency of inhomogeneities of $<50\times 10^{+9}$ m$^{-2}$.

The inhomogeneities belong to one or more of the following categories:

a) cracks and/or porous regions along the boundaries of powder aggregates/powder agglomerates, b) nest-like regions in the microstructure having a loosened structure with many pores, c) pores having a diameter exceeding twice the grain size.

Inhomogeneities of the following category may also be taken into account:

d) grains of >10 μm and/or agglomerates of individual grains having an agglomerate size of greater than 10 μm and a diameter which exceeds five times the mean grain size.

In addition, all pores having a diameter of $\geq 0.3$ μm may be taken into account in the case of the inhomogeneities of the category c).

The frequency of the inhomogeneities is advantageously $\leq 20\times 10^{+9}$ m$^{-2}$. In contrast, in the case of sintered corundum of the prior art, the frequency of the inhomogeneities is more than $50\times 10^{+9}$ m$^{-2}$.

Advantageously, even sintered microstructures having mean grain sizes below 0.8 μm can be obtained using the process of the invention.

The sintered material advantageously has a microstructure having a predominantly irregular orientation of the crystallites.

In a further embodiment of the invention, importance is attached to achieving both a comparatively high hardness and a high flexural strength. The additional requirement of a high flexural strength in this embodiment requires a sintered material which also has a certain size distribution of the defects or inhomogeneities as qualifying feature. This in turn requires the characterization of the sintered material of the invention by means of a dimensionless defect density defined as the sum of the squares of the defect sizes per area analysed, as was originally introduced for the evaluation of microcrack densities (A. Krell et al., J. Mater. Sci. (1987)9, 3304–08). Here, the defect size employed is the maximum recognizable extent of the defect in any direction in the analysed plane. In the case of ceramic materials of the prior art, the frequency of such inhomogeneities is more than $30\times 10^{-3}$. The further embodiment of the invention is characterized by a content of from 95 to 100% by volume of $Al_2O_3$ and a Vickers low-load hardness of $\geq 1750$ at a test load of from 10 N to 100 N (HV1 to HV10) and a flexural strength of $\geq 800$ MPa, with the sintered material having a relative sintered density of $\rho \geq 98.5\%$, a microstructure with a mean grain size of $\leq 2$ μm and a dimensionless defect density of $<30\times 10^{-3}$, where the defects belong to one or more of the following categories:

a) cracks and/or porous regions along the boundaries of powder aggregates/powder agglomerates, b) nest-like regions in the microstructure having a loosened structure with many pores, c) pores having a diameter exceeding twice the mean grain size, d) grains of >10 μm and/or agglomerates of individual grains having an agglomerate size of greater than 10 μm and a diameter which exceeds five times the mean grain size.

The microstructure of the sintered material which combines high hardness with high flexural strength also advantageously has a predominantly irregular orientation of the crystallites.

The sintered products of the invention can also contain, in addition to corundum ($\alpha$-$Al_2O_3$), up to 5% by volume of other substances as long as the abovementioned permissible limits of the relative density, the frequency of the inhomogeneities mentioned or the dimensionless defect density are still adhered to. The fracture toughness ($K_{Ic}$) of the products of the invention can considerably exceed the level typical for sintered corundum, depending on measurement method between about 3 and 4.5 MPa√m. However, this is not a condition for implementing the invention. For determining the fracture toughness, it has to be noted that, in particular, the measurement method used has a strong and difficult-to-quantify influence on the measured value found, so that measured values can frequently not be compared with one another.

A process for producing a sintered $Al_2O_3$ material of the invention comprises the following steps:

a) conversion of an $\alpha$-$Al_2O_3$ powder having a mean particle size $d_{50}$ of $\leq 0.30$ μm and a chemical purity of ≧99.9% of $Al_2O_3$ in a liquid into a stable suspension of dispersed particles by means of simultaneous and/or sequential use of at least two different dispersing methods, b) production of an unsintered precursor having a relative density of $\rho \geq 55\%$ by means of shaping, c) heat treatment and sintering of the precursor.

The process of the invention does not require use of very expensive powders of uniform ("monosized", "uniform-sized") particle size, but rather it can be advantageously carried out using a very much cheaper $\alpha$-$Al_2O_3$ powder having the following particle size distribution: $d_{16} > 0.065$ $\mu m$, $d_{50} \leq 0.30$ $\mu m$, $d_{84} \leq 0.45$ $\mu m$. This is a particular advantage of the invention since it makes possible the production of correspondingly high-value sintered materials at lower cost than in the case of the prior art. Essential to the success of the production process of the invention is the preparation of a stable (and particularly homogeneous) suspension of the dispersed particles by simultaneous and/or sequential use of at least two different dispersing methods.

Advantageously, the $\alpha$-$Al_2O_3$ powder used in step a) has a specific surface area, determined by the BET method of from 10 to 17 $m^2/g$.

The abovementioned particle size distribution of the $\alpha$-$Al_2O_3$ starting powder used is of particular importance to the success of the invention. Larger mean particle sizes than permissible, higher amounts of coarse material ($d_{84}$ shifted to higher values) and correspondingly lower specific surface areas reduce the sintering activity, increase the sintering temperature required and thus lead to unacceptable coarse microstructures. Smaller mean particle sizes or higher amounts of very fine material ($d_{16}$ shifted to lower values) cause problems in the subsequent shaping and sintering: the resulting reduced green density (i.e. the density of the unsintered products) and an increased defect frequency likewise require increased sintering temperatures, so that coarser sintered products having more inhomogeneities and defects are formed. A reduced purity of the powder raw material below the value indicated according to the invention leads, at least locally, to formation of liquid phases during sintering, so that the microstructures produced contain amorphous grain boundary phases, precipitates, micropores and other undesired microdefects. Even when amorphous phases cannot be detected, a reduction of the powder purity to be adhered to according to the invention leads to uncontrollable grain growth processes during sintering.

To produce a sintered $\alpha$-$Al_2O_3$ material in which importance is not exclusively attached to a particularly high hardness, but in which a high flexural strength is sought at the expense of a somewhat reduced hardness, the production process of the invention can be modified so as to employ the following steps:

a) conversion of an $\alpha$-$Al_2O_3$ powder having a particle size distribution determined by the parameters $d_{16} > 0.065$ $\mu m$, 0.2 $\mu m \leq d_{50} \leq 0.4$ $\mu m$, 0.45 $\mu m \leq d_{84} \leq 0.8$ $\mu m$ and a chemical purity of $\geq 99.9\%$ of $Al_2O_3$ in a liquid into a stable suspension of dispersed particles by means of simultaneous and/or sequential use of at least two different dispersing methods, b) production of an unsintered precursor having a relative density of $\rho \geq 55\%$ by means of shaping, c) heat treatment and sintering of the precursor.

The difference between this and the first-mentioned process is that a slightly higher mean particle size and a somewhat higher proportion of coarse material may be permissible. It is thus possible to use an even more inexpensive starting material. Here too, mean particle sizes which are larger than permissible, higher proportions of coarse material ($d_{84}$ shifted to higher values) and correspondingly lower specific surface areas reduce the sintering activity, increase the sintering temperature in an unacceptable way and thus lead to microstructures which are too coarse-grained to achieve the abovementioned mechanical properties. Higher proportions of very fine material ($d_{16}$ shifted to lower values) and a reduced purity of the powder raw material here also cause the same problems as discussed above.

The $\alpha$-$Al_2O_3$ powder used as starting material in this modification of the production process of the invention advantageously has a specific surface area determined by the BET method of 8–17 $m^2/g$.

The sintering processes used for the purposes of the invention can be pressureless or employ pressure (e.g. hot pressing or hot isostatic pressing). However, a particular advantage of the invention is that $\alpha$-$Al_2O_3$ materials of high hardness and/or strength are also obtained when using pressureless sintering processes.

In this context, it may be pointed out that pressureless sintering in air compared with hot pressing or hot isostatic pressing (HIPping) leads, owing to the differences in the surrounding atmosphere (in particular the oxygen partial pressure), to considerable structural differences which in turn alter diffusion coefficients and mechanical, optical and electrical properties dependent thereon (S. K. Mohapatra et al., J. Am. Ceram. Soc. (1978), Issue 3/4, 106–109; S. K. Mohapatra et al., J. Am. Ceram. Soc. (1979), Issue 1/2, 50–57).

Hot pressing or hot isostatic pressing are usually carried out in a protective gas atmosphere (argon), so that there is a reduced oxygen partial pressure and, on the other hand, the carbon-containing materials used for the purposes of the pressing process result in a CO partial pressure which has a reducing action which produces oxygen vacancies as point defects distributed over the entire corundum lattice and leading to the abovementioned changed properties. Among other things, there results a dark grey coloration of the corundum in contrast to the typical pale appearance of sintered $Al_2O_3$ materials produced by pressureless sintering in air (T. Nagatome et al., J. Ceram. Soc. Japan, Int. Ed. (1994), Issue 1, 147–151).

For both variants of the production process, the dispersing methods employed in step a) are advantageously selected from the following group:

mechanical stirrer, treatment with ultrasound, use of a ball mill.

When a ball mill is employed, its milling action is of lesser importance than its mixing and thus dispersing action on the material being milled, any powder agglomerates formed are also destroyed. It may be remarked that this listing of the dispersing methods is not exhaustive and other suitable dispersing methods can likewise be used. However, the invention has recognized that the use of a single dispersing method is in no case sufficient for carrying out the process of the invention and for producing $\alpha$-$Al_2O_3$ materials which are in accordance with the invention.

The starting powder of a defined nature which is to be used according to the invention is converted in a liquid, preferably in distilled or deionized water having a pH in the range 3–7, preferably 4–6, more preferably about 5, to which dispersants customary for the dispersion of $\alpha$-$Al_2O_3$ powders can be added in the form of mineral acids, carboxylic acids, polycarboxylic acids or other polyelectrolytes, into a stable finely divided suspension. This is achieved by a synergistic combination of different dispersing methods, e.g. by the abovementioned combined use of a high-speed stirrer, ultrasound or ball mills. This intensive dispersing achieves a high stability of the essentially agglomerate-free suspension in a pH range as high as 3–7, while, according to widespread opinion, a sufficient degree of dispersion for the finely divided powders of the type with which the invention is exclusively concerned is achieved only at a pH of <3 (T. Kimura et al., Sci. Sintering (1990) 2, 59–64). However, such low pH values bring with them not only corrosive stress on the machines and containers but also additional disadvantages for the quality of the slip (e.g. the viscosity can rise as a result of, inter alia, dissolution processes and force a restriction to low solids contents).

To intensify the densification process and to control the development of the microstructure during sintering, chemical substances which usually contain elements such as Mg or else Li, Ba, Sr, Zn, Fe, Co, Ni, Cr, Zr, Ti, Si, Y, Ce, La or Y can be added to the dispersion for the purposes of the process of the invention up to a total concentration of 0.5% by mass (based on the $Al_2O_3$). However, the finely divided starting powder of a defined nature to be used according to the invention leads to a structure of the green intermediate products which is such that on sintering the grain growth-inhibiting action of substances such as Mg is slight (and largely unnecessary); it can, however, still be detected in many cases.

The slip thus produced is processed to an initially unsintered precursor having a relative density of >55% either using pressure or by pressureless casting processes.

The processes using pressure which can be employed fall into 2 groups: binder-free processes such as pressure filtration and processes in which binders and pressing aids are additionally added to the slip during the intensive dispersing procedure (cold isostatic pressing, extrusion, injection moulding).

Particularly high hardnesses are achieved when the grain size of the sintered $Al_2O_3$ products of the invention having a relative density of $\geq 98.5\%$ is advantageously reduced to less than 0.8 $\mu$m and at the same time a particularly homogeneous microstructure build-up which avoids inhomogeneities in the form of pore structures of any type is achieved. A particularly advantageous process for producing such sintered products comprises pressure filtration of slips as described above produced according to the invention, where the slips have a solids content of at least 60% by mass, followed by cold isostatic pressing of the body previously dried to a residual moisture content of advantageously 0.5–3%. The pressure in the pressure filtration is between 0.3 and 20 MPa, advantageously in the region of 3.5 ($\pm$ about 2) MPa; for the further compaction by means of cold isostatic pressing, a pressure of $\geq 200$ MPa is sufficient.

In the sintering process, shaped bodies thus produced reach relative densities of 99% even at temperatures from 1200–1250° C.; the mean grain sizes can be reduced to the region of about 0.4 $\mu$m. Ground products of this type have, for example, hardnesses of HV1>2300, the strengths achieved are in the range of about 650–750 MPa.

A particularly economical process comprises producing low-defect sintered $\alpha$-$Al_2O_3$ bodies of the invention having Vickers low-load hardnesses of >2000 at a relative sintered density of $\geq 98.4\%$ and mean grain sizes of $\leq 1.5$ $\mu$m, in particular mean grain sizes in the range 0.6–0.9 $\mu$m, by preparing a slip according to the invention as described above from dispersed corundum powder of a defined nature, adding a pressing aid and converting the slip into a granular material, then shaping green bodies using cold isostatic pressing, which is widespread in the ceramics industry, at a relatively low pressure of $\geq 200$ MPa; it is advantageous to employ prepressing (e.g. uniaxial) at a low pressure of 20–200 MPa, particularly preferably in the region of 40 ($\pm$ about 10) MPa. A prerequisite is the conversion of the slip into a granular material which on pressing gives virtually no agglomerates of powder particles in the green shaped body. The granular material is optimized by mutual matching of the generally known binders added and the drying and granulation regime.

A particularly advantageous process, which can be applied to any shape, for producing extremely low-defect sintered $Al_2O_3$ products of the invention having high strengths of more than 800 MPa and high Vickers low-load hardnesses of more than 1750 at a relative density of $\geq 98.5\%$ and mean grain sizes of $\leq 2$ $\mu$m comprises pressureless casting of the slip and subsequent consolidation by coagulation processes, by in situ polymerization of an added monomer or the like. In the case of consolidation by polymerization, a polymerizable monomer, e.g. acrylamide or hydroxyethyl acrylate, and a polymerization initiator, e.g. ammonium persulphate, are added to an aqueous $Al_2O_3$ dispersion which has been adjusted to a solids content of >60% by mass, typically 70–85% by mass. In the procedure according to the invention for producing extraordinarily low-defect sintered products of the invention from a finely divided corundum powder of the defined granulometric nature described, it is of critical importance, on the one hand, that the corundum powder is particularly carefully intensively dispersed together with the monomer and also that the slip is subsequently degassed (advantageously aided by ultrasound) at a reduced pressure of 100–300 mbar before the commencement of polymerization.

After degassing, the slip is poured into moulds and polymerized in a nitrogen atmosphere either by addition of a catalyst or by increasing the temperature to 55–80° C.

For all shaping variants, the shaped bodies can be dried for 2–3 days in air and subsequently in a drying oven at 70–110° C.; the required duration of the drying process is shorter for lower moisture contents of the products. It is particularly advantageous to carry out drying in a drying oven with temperature and humidity regulation, with the heating rate to 90° C. being 1–2 K/h and the humidity in the oven being reduced simultaneously from 60–80% to 15–20%. After a hold time of 4–6 hours at 90° C., the products are cooled to room temperature while maintaining the low humidity in the oven.

If desired, further compaction by cold isostatic pressing can be provided. In this case, the green body should be adjusted to a residual moisture content of 0.5–3% before this further compaction.

The relative density of the dried specimens is $\geq 55\%$ of the theoretical density, preferably $\geq 60\%$.

The dried specimens are subjected to a thermal treatment at 700–900° C. in air, with the heating rate being from 0.1 to 0.3 K/min and the hold time in the thermal treatment being 1–4 hours.

Sintering is carried out at a temperature between 1200 and 1500° C. in air, with the heating rate being 1–3 K/min and the hold time at the sintering temperature being 0.5–8 hours.

Products thus produced can achieve high strengths even with a relatively coarse microstructure having grain sizes between 1 and 2 $\mu$m. For example, a mean flexural strength of 862 MPa was measured at a mean grain size of 1.31 $\mu$m.

The very great strength gain achieved in the field of this casting technology by means of the process steps of the invention compared with the previous strengths of not more than 400 MPa according to the prior art (A. C. Young, et al., J. Am. Ceram. Soc. (1991)3, 612–618; R. Wäsche et al., cfi/Ber.DKG (1995) 1/2, 24–27) is a particularly surprising result of the invention.

In view of the comprehensive known prior art and the fact that it was hitherto accepted as self-evident, in accordance with statements such as those of Skrovanek et al., that a grain size below 3–4 $\mu$m did not further increase the hardness of sintered corundum, it was extraordinarily surprising that sintered products having a Vickers low-load hardness of $\geq$2000 at a test load of from 10 N to 100 N (HV1 to HV10) or having a Vickers low-load hardness of $\geq$1750 and a flexural strength of $\geq$800 MPa could be specified and obtained by producing microstructures having a mean grain size of $\leq$1.5 $\mu$m or $\leq$2 $\mu$m and a relative sintered density of $\rho \geq$98.5%.

The studies have shown, as has the known prior art, that a relative sintered density as stated according to the invention or a small grain size in a sintered product are themselves not sufficient to produce a higher hardness. Only the combination of a grain size of 1.5 $\mu$m with a relative sintered density $\rho \geq$98.5% and the avoidance of inhomogeneities and defects having a frequency and density in the sintered product exceeding fixed upper limits lead to this high Vickers low-load hardness and strength.

A particular advantage of the process of the invention is that it is useful for technologies wide-spread in the ceramic industry, which technologies in this way make possible the production of even relatively large, very low-defect shaped bodies of defined geometric dimensions and high hardness.

The said properties of the novel sintered $Al_2O_3$ products made from corundum powder make possible their advantageous use under very different, demanding industrial conditions. Thus, their very high hardness and simultaneously high strength make possible increased reliability in medical implants, improve the wear resistance of wear products, for example of cutting tools or other tools or parts thereof, of wear-resistant components in machines, valves, pumps, bearings, of thread guides, guide elements and deflector elements, of substrates for microelectronic applications, of computer disks and increase the abrasion performance achieved with sintered corundum abrasives of this type. The materials of the invention can be advantageously used in the form of sintered grains (for example bonded to substrates or in abrasive bodies) as grinding or polishing means.

The invention is illustrated below by means of a number of examples. Example 1 illustrates the best embodiment for a product of very high hardness, Example 4 describes a product of particularly favourable design for combining high hardness and strength.

EXAMPLE 1

150 g of a finely divided $\alpha$-alumina having a narrow particle size distribution, viz. Taimicron TM-DAR ($d_{16}$=0.13 $\mu$m, $d_{50}$=0.19 $\mu$m, $d_{84}$=0.25 $\mu$m, BET=14 $m^2$/g), were dispersed for 30 minutes in an aqueous solution comprising 120 ml of distilled water, 9 ml of 10% strength polyvinyl alcohol solution and 3 ml of glycerol by means of a high-speed stirrer (5000 rpm).

The dispersion was subsequently milled for 1 hour in a laboratory stirred ball mill using YTZP milling media at a stirrer speed of 1000 rpm and thereby homogenized and further dispersed and then subjected to freeze drying.

The mixture freeze-dried to a residual moisture content of <2% was brushed through a 300 $\mu$m sieve and precompacted uniaxially at 30 MPa to give a shaped body. The shaped body was subsequently cold isostatically pressed in a thin elastic envelope at 700 MPa. After drying at 80° C., the relative density achieved was 61.0% of the theoretical density.

The shaped body was subjected to preliminary firing at 800° C. in air (heating race 0.3 K/min, 1 hour hold time at 800° C.) and subsequently pressureless sintered in air at 1400° C. (heating rate 2 K/min, hold time 2 hours at sintering temperature, furnace cooling).

The defect analysis was carried out by means of scanning electron microscopy on polished surfaces thermally etched at 1300° C. Defects in the sintered product typically appeared in the form of individual pores having a size of 0.3–30 $\mu$m and a low frequency of $8 \times 10^{+9}$ $m^{-2}$; the dimensionless defect density, which takes into account the defect size distribution, was $10 \times 10^{-3}$. In contrast, sintered bodies produced from the same raw material according to the prior art by dry pressing and sintering showed a frequency of such microstructural inhomogeneities of $40 \times 10^{+9}$ $m^{-2}$ or a dimensionless defect density of $96 \times 10^{-3}$. When the evaluation was restricted to pores of $\geq$1.3 $\mu$m (= double the mean grain size), a substantially lower frequency of $0.85 \times 10^{+9}$ $m^{-2}$ was measured in the product of the invention, which, on comparison, indicates a very large number of small pores of <1 $\mu$m.

The density was determined by means of the buoyancy method. Grain size characterization was carried out as an intercepted segment analysis on polished and thermally etched surfaces (grain size=1.56×mean chord length).

The mechanical property tests were, with the exception of the wear tests, carried out on ground flexural test bars (diamond grinding wheel 40/50 $\mu$m/wet grinding/feed increment 0.01–0.02 mm), which is particularly useful for the determination of application-oriented hardness data, since ground parts are predominantly employed in industrial use. The bars were cut beforehand from the sintered shaped bodies by means of cutting wheels.

For comparison, hardness values for polished surfaces are indicated.

The wear measurements were carried out on polished surfaces in water under the action of an $Al_2O_3$ ball oscillating in a straight line (grain size 15 $\mu$m, ball radius R=5 mm, applied force $F_N$=10 N, frequency 20 Hz, rubbing path x=0.2 mm). Without normalization to the applied force, which at the widths of the wear track typical here under steady-state conditions generates a pressure in the range of 100–300 MPa, a wear coefficient can be defined as V=$\pi$b/(64 R·2x·n) (b: width of the wear track formed, n: number of cycles, here n=100,000).

The following property values were determined.

| | |
|---|---|
| Density: | 3.941 g/cm$^3$ (absolute) |
| | 98.9% (relative) |
| Mean grain size: | 0.65 $\mu$m |
| Hardness | |
| HV10: | 2258 ± 101 |
| HV3: | 2514 ± 124 |
| HV1: | 3055 ± 208 |
| Hardness of the polished surface | |
| HV10: | 2055 ± 94 |
| Fracture strength: (3-point bend) | 653 ± 32 MPa. |
| Wear coefficient V: | 8 × 10$^{-7}$ mm$^3$/m. |

Comparative tests using an isostatic pressing pressure reduced to 350 MPa led to sintered products whose hardness values were not significantly different from the above results.

The hardness result can be evaluated by comparison with ground comparative flexural test bars of $Al_2O_3$+35% by volume of TiC produced by hot isostatic pressing and having a density of 99% and a mean grain size of 1.7 μm. For these comparative specimens, the following values were determined:

| Hardness | |
|---|---|
| HV10: | 2290 ± 76 |
| HV3: | 2386 ± 173 |
| HV1: | 2510 ± 192. |

In this evaluation, the sintered $Al_2O_3$ bodies of the invention comprising sintered corundum, which had been produced by pressureless sintering in air, displayed a hardness which equals and even exceeds that of hot isostatically pressed composites having a high proportion of hard material.

In contrast, the hardness and flexural strength of the comparative sintered corundum specimens with their above-mentioned higher defect density corresponded, with their values of only HV10=1762±53 and $\sigma_{bB}$=400±60 MPa, to that expected for microstructures according to the prior art.

To evaluate the wear figure, comparison may be made with the requirements of the international standard ISO-6474 for $Al_2O_3$ implant materials. In a likewise oscillating wear test (different arrangement at only 20 MPa applied pressure), this standard requires a time-based wear of less than 0.01 $mm^3$/h, which corresponds to a limit of $2 \times 10^{-4}$ $mm^3$/m based on the wear path of the test arrangement. In comparison, the wear found in the example examined here is three orders of magnitude lower despite an applied pressure which is higher by a factor of 10.

EXAMPLE 2

200 g of a particle size fraction ($d_{16}$=0.09 μm, $d_{50}$=0.12 μm, $d_{84}$=0.16 μm) obtained from the α-alumina Taimicron TM-DAR by centrifugal classification were introduced while stirring into 80 ml of distilled water which had been brought to pH=5 using 1 N $HNO_3$, with the pH being continually readjusted to 5 during the addition.

The suspension was then intensively dispersed for a further 1 hour by means of a stirrer and simultaneous ultrasound treatment, sieved through a 30 μm sieve and pressed at 3.5 MPa in a pressure filtration cell with a 0.1 μm membrane filter to give discs having a diameter of 60 mm and a thickness of 6 mm.

The shaped bodies were dried stepwise between 20 and 80° C. over a period of 3 days to a residual moisture content of from 2 to 3%, then further compacted by cold isostatic pressing in elastic envelopes at 700 MPa and again dried for 5 hours at 80° C., which led to a relative density of 60.2% of the theoretical density.

The shaped bodies were then subjected to preliminary firing at 800° C. in air (heating rate 0.3 K/min, 1 hour hold time at 800° C.) and pressureless sintered at 1350° C. (heating rate 2 K/min, 2 hours hold time at sintering temperature, furnace cooling).

Microstructural studies on the ceramic showed only scattered small pores having a size of 0.3–5 μm and a frequency of $2 \times 10^{+9}$ $m^{-2}$, the dimensionless defect density was $4 \times 10^{-3}$. When the evaluation was restricted to pores of $\geq 0.8$ μm (= double the mean grain size), a frequency of $3 \times 10^{+9}$ $m^{-2}$ was found, which was identical within the accuracy of the measurements.

The specimen preparation and characterization were carried out as in Example 1.

The following property values were determined:

| | |
|---|---|
| Density: | 3.940 g/cm³ (absolute) |
| | 98.8% (relative) |
| Mean grain size: | 0.40 μm |
| Hardness HV10: | 2286 ± 74 |
| Wear coefficient V: | $5 \times 10^{-7}$ mm³/m |

EXAMPLE 3

370 g of α-$Al_2O_3$ powder of the type Taimicron TM-DAR were mixed while stirring into a mixture of 80 ml of distilled water, 3.7 ml of dispersant Dolapix CE64 (carboxylic acid preparation from Zschimmer und Schwarz GmbH & Co. Chemische Fabriken, Lahnstein, Germany) and 18.5 ml of $Mg(NO_3)_2$ solution (containing 1.18 g of $Mg(NO_3)_2 \cdot 6HO$)

The suspension was then intensively dispersed for a further 1 hour by means of a stirrer and simultaneous ultrasound treatment, sieved through a 30 μm sieve and pressed at 3.5 MPa in a pressure filtration cell with a 0.1 μm membrane filter to give discs having a diameter of 60 mm and a thickness of 6 mm.

The shaped bodies were dried stepwise between 20 and 110° C. over a period of 3 days, which led to a relative density of 61.5%. The shaped bodies were then subjected to preliminary firing at 800° C. in air (heating rate 0.3 K/min, 1 hour hold time at 800° C.) and pressureless sintered at 1275° C. in air (heating rate 2 K/min, 2 hours hold time at sintering temperature, furnace cooling).

The microstructural analysis of the sintered product showed individual pores of $\geq 0.3$ μm at a frequency of $2 \times 10^{+9}$ $m^{-2}$ (dimensionless defect density is $0.6 \times 10^{-3}$) and additional nest-like collections of pores having a frequency of $7 \times 10^{+8}$ $m^{-2}$; the typical size of these porous regions was from 3 to 50 μm (in further optimized processes of this type not described here, these nest-like porous regions could be avoided). When the evaluation of individual pores was restricted to sizes of $\geq 1.5$ μm (= double the mean grain size), a distinctly reduced frequency of $0.2 \times 10^{+9}$ $m^{-2}$ was measured, as had already been found in Example 1.

The specimen preparation and characterization were carried out as in Example 1.

The following property values were determined:

| | |
|---|---|
| Density: | 3.947 g/cm³ (absolute) |
| | 99.0% (relative) |
| Mean grain size: | 0.76 μm |
| Hardness HV10: | 2362 ± 85 |
| Hardness of the polished surface: | |
| Hardness HV10: | 2105 ± 57 |

EXAMPLE 4

19.2 g of acrylamide and 0.8 g of N,N'-methylenebis (acrylamide) were introduced together with 250 g of α-$Al_2O_3$ powder of the type Taimicron TM-DAR into 75 ml of distilled water and intensively dispersed for 2 hours by means of a stirrer and simultaneous ultrasound treatment, with the pH being adjusted to 4 using dilute nitric acid. After addition of 0.06 g of $(NH_4)_2S_2O_8$ dissolved in 10 ml of $H_2O$, the slip was poured into a glass dish to give an 8 mm thick layer and was first degassed at room temperature in a vacuum drying oven at 200 mbar. The polymerization of the acrylamide was then carried out under a nitrogen atmosphere by increasing the temperature to 60° C. After holding for one hour and slowly cooling to room temperature, the disc-shaped body was taken out and dried in air in an air-conditioned cabinet over a period of two days while uniformly increasing the temperature from 25 to 90° C. and simultaneously reducing the relative humidity from 60 to 15%.

The shaped bodies were subjected to preliminary firing at 800° C. in air (heating rate 0.3 K/min, 1 hour hold time at 800° C.), which led to a green density of 58.4% of the theoretical density. The shaped bodies were subsequently pressureless sintered at 1300° C. (heating rate 2 K/min, 2 hours hold time at sintering temperature, furnace cooling).

The specimen preparation and characterization were carried out as in Example 1.

Microstructural studies on the ceramic in a scanning electron microscope. showed scattered small pores with typical sizes of less than 3 $\mu$m, the upper limit for the size of the pores is in the region of 10 $\mu$m. The overall frequency of the inhomogeneities observed is only $2.2\times10^{+9}$ $m^{-2}$; taking the defect sizes into account, a dimensionless defect density of $3\times10^{-3}$ was determined.

The following property values were determined:

| Density: | 3.968 g/cm³ (absolute) |
| --- | --- |
| | 99.5% (relative) |
| Mean grain size: | 1.15 $\mu$m |
| Hardness HV10: | 2143 ± 51 |
| Fracture strength: | 810 ± 43 MPa. |
| (3-point bend) | |

EXAMPLE 5

Example 4 was repeated except that the intermediate product after the polymerization was dried in air at room temperature and subsequently subjected to further compaction by cold isostatic pressing at a pressure of 700 MPa. Although no significant change in the green density could be detected, the following changes compared with Example 4 were achieved:

the frequency of inhomogeneities observed is, at $0.2\times10^{+9}$ $m^{-2}$, lower by a factor of ten than in Example 4, while the dimensionless defect density, which takes into account the defect sizes, was at $4\times10^{-3}$ not significantly different from that in Example 4, a sintered density of 3.961 g/m³, corresponding to 99.3%, was reached under a sintering condition of only 1275° C./2 h, the mean grain size of the sintered microstructure was 0.97 $\mu$m, improved reliability in the form of a reduced standard deviation of the flexural strength: 822±19 MPa;

the hardness of HV10=2112±39 was not significantly different from that in Example 4.

EXAMPLE 6

Example 6 corresponds largely to the process of Example 2, but carried out using a somewhat coarser powder raw material. 372 g of an α-alumina having a specific surface area determined by the BET method of 10.5 m²/g and a particle size distribution described by $d_{16}$=0.2 $\mu$m, $d_{50}$=0.3 $\mu$m, $d_{84}$=0.6 $\mu$m were introduced while stirring into 80 ml of distilled water which had been brought to pH=4 using 1 N $HNO_3$.

The suspension was then intensively dispersed for a further 1 hour by means of a stirrer and simultaneous ultrasound treatment, sieved through a 20 $\mu$m sieve and pressed at 1 MPa in a pressure filtration cell with a 0.2 $\mu$m membrane filter to give discs having a diameter of 125 mm and a thickness of 6 mm.

The shaped bodies were dried stepwise between 20 and 90° C. over a period of 2 days to a residual moisture content of 1–2%, then further compacted by cold isostatic pressing in elastic envelopes at 700 MPa and again dried for 5 hours at 90° C., which led to a relative density of 64% of the theoretical density.

The shaped bodies were then subjected to preliminary firing at 800° C. in air (heating rate 0.3 K/min, 1 hour hold time at 800° C.) and pressureless sintered at 1450° C. (heating rate 2 K/min, 2 hours hold time at sintering temperature, furnace cooling). The defect density determined subsequently was $4\times10^{-3}$.

The specimen preparation and characterization were carried out as in Example 1.

The following property values were determined:

| Density: | 3.960 g/cm³ (absolute) |
| --- | --- |
| | 99.3% (relative) |
| Mean grain size: | 1.7 $\mu$m |
| Hardness HV10: | 1790 ± 48 |
| Fracture strength: | 807 ± 67 MPa. |
| (3-point bend) | |

EXAMPLE 7

The unsintered precursor from Example 1 was crushed in a jaw crusher after the preliminary firing and classified. The fraction in the range 0.2–2 mm was sintered for 2 hours in air at 1465° C. The sintered product having a density of 3.948 g/cm³, corresponding to 99.0% of the theoretical density, was classified and the 0.4–0.7 mm fraction was applied by means of a binder to a flexible grinding disc and compared in terms of its grinding performance with two types of fused alumina in the following test:

Workpiece: Welded steel tube of scale-free, cold-rolled sheet (St W 22 DIN 1543), diameter 160 mm, wall thickness 1 mm.

Grinding conditions: rotation speed of disc 6000 rpm, rotational speed of tube 16.3 rpm corresponding to a circumferential speed of 10 m/min, applied force 30 N.

Test parameter: amount of steel abraded (measured in gram) after from 1 to 4 minutes.

A high grinding performance is indicated by a high amount of material abraded from the workpiece. After 1, 2, 3 and 4 minutes respectively, the following total amounts of abraded material were measured:

Normal corundum: 41 g (1 min)–64 g (2 min)–83 g (3 min)–99 g (4 min).

Eutectic zirconia-containing alumina: 49 g (1 min)–76 g (2 min)–99 g (3 min)–119 g (4 min).

Sintered corundum, according to the invention: 79 g (1 min)–142 g (2 min)–188 g (3 min)–226 g (4 min).

On a time-average basis, the results represent a performance increase for the product of the invention of 217% compared with the normal corundum or of 182% compared with the zirconia-containing alumina material.

We claim:

1. A method, comprising the steps of:
   a) dispersing α-$Al_2O_3$ powder having a mean particle size $d_{50}$ of ≦0.30 μm and a chemical purity of ≧99.9% α-$Al_2O_3$ in an aqueous solution to create a mixture, said mixture effected through the application of at least two different dispersing methods;
   b) treating said mixture so as to create a shaped unsintered body having a relative density of p≧55%;
   c) heating said unsintered body; and
   d) sintering said unsintered body so as to create a sintered material.

2. A method, comprising the steps of:
   a) dispersing α-$Al_2O_3$ powder having a mean particle size $d_{50}$ of ≦0.30 μm and a chemical purity of ≧99.9% $Al_2O_3$ in an aqueous solution comprising water, polyvinyl alcohol and glycerol to create a mixture;
   b) treating said mixture so as to create a shaped unsintered body having a relative density of p≧55%;
   c) heating said unsintered body; and
   d) sintering said unsintered body so as to create a sintered material.

3. The method of claim 1, wherein said dispersing methods are selected from the group consisting of stirring, milling, and ultrasound.

4. The method of claim 1, wherein said α-$Al_2O_3$ powder of step (a) has a specific surface area of 10–17 $m^2$/g.

5. The method of claim 1, wherein said sintering comprises pressureless sintering in air.

6. The sintered material produced according to claim 1, wherein said sintered material comprises a mean grain size of 1.5 μm or less, a density of no less than 98.5% of a theoretical density, and a Vickers hardness greater than or equal to 2,000 at a test load from 10 to 100 N, said sintered material having a frequency of inhomogeneities of less than $50 \times 10^9$ $m^{-2}$.

7. A method, comprising the steps of:
   a) dispersing α-$Al_2O_3$ powder having a particle size of $d_{16}$ greater than 0.065 μm, $d_{50}$ not less than 0.2 μm and not greater than 0.4 μm, $d_{84}$ not less than 0.45 μm and not greater than 0.8 μm, and a chemical purity of ≧99.9% α—$Al_2O_3$, in an aqueous solution to create a mixture, said mixture effected through the application of at least two different dispersing methods;
   b) treating said mixture so as to create a shaped unsintered body having a relative density of p≧55%;
   c) heating said unsintered body; and
   d) sintering said unsintered body so as to create a sintered material.

8. The method of claim 7, wherein said mixture in step (a) has a pH of between 3 and 7.

9. The method of claim 7, wherein said mixture in step (a) has a pH of between 4 and 6.

10. The method of claim 7, wherein said mixture in step (a) has a pH of approximately 5.

11. The method of claim 7, wherein said mixture further comprises chemical substances containing one or more elements selected from the group consisting of Li, Mg, Ba, Sr, Zn, Fe, Co, Ni, Cr, Zr, Ti, Si, Y, Ce, La and Y.

12. The method of claim 7, wherein said dispersing methods are selected from the group consisting of stirring, milling, and ultrasound.

13. The method of claim 7, wherein said sintering comprises pressureless sintering in air.

14. The sintered material produced according to claim 7, wherein said sintered material comprises a mean grain size of 2.0 μm or less, a density of no less than 98.5% of a theoretical density, a Vickers hardness greater than or equal to 1,750 at a test load from 10 to 100 N, and a flexural strength of 800 MPa or greater, said sintered material having a dimensionless defect density of less than $30 \times 10^{-3}$.

15. A method, comprising the steps of:
   a) dispersing α-$Al_2O_3$ powder having a mean particle size $d_{50}$ of ≦0.30 μm and a chemical purity of ≧99.9% $Al_2O_3$ in an aqueous solution to create a mixture, said dispersing comprising stirring said solution and subsequently milling;
   b) treating said mixture so as to create a shaped unsintered body having a relative density of p≧55%;
   c) heating said unsintered body; and
   d) sintering said unsintered body so as to create a sintered material.

16. The method of claim 15, wherein said α-$Al_2O_3$ powder of step (a) has a specific surface area of 10–17 $m^2$/g.

17. The method of claim 15, wherein said sintering comprises pressureless sintering in air.

18. The sintered material produced according to claim 15, wherein said sintered material comprises a mean grain size of 1.5 μm or less, a density of no less than 98.5% of a theoretical density, and a Vickers hardness greater than or equal to 2,000 at a test load from 10 to 100 N, said sintered material having a frequency of inhomogeneities of less than $50 \times 10^9$ $m^{-2}$.

19. A method, comprising the steps of:
   a) dispersing α-$Al_2O_3$ powder having a chemical purity of ≧99.9% $Al_2O_3$ in an aqueous solution to create a mixture, said dispersing comprising stirring said solution and simultaneously subjecting said solution to ultrasound;
   b) treating said mixture so as to create a shaped unsintered body;
   c) heating said unsintered body; and
   d) sintering said unsintered body so as to create a sintered material.

20. The method of claim 19, wherein said aqueous solution comprises water and one or more dispersants selected from the group consisting of mineral acids, carboxylic acids and polycarboxylic acids.

21. The method of claim 19, wherein said treating of step (b) comprises pressure filtration.

22. The method of claim 19, wherein the treated mixture is dried such that a residual moisture content of between 2% and 3% is achieved.

23. The method of claim 19, wherein said sintering comprises pressureless sintering in air.

24. The sintered material produced according to claim 19, wherein said sintered material comprises a mean grain size of 1.5 μm or less, a density of no less than 98.5% of a theoretical density, and a Vickers hardness greater than or equal to 2,000 at a test load from 10 to 100 N, said sintered material having a frequency of inhomogeneities of less than $50 \times 10^9$ $m^{-2}$.

25. Sintered $Al_2O_3$ material comprising a mean grain size of 1.5 μm or less, a density of no less than 98.8% of a theoretical density, and a Vickers hardness greater than or equal to 2,160 at a test load from 10 to 100 N, said sintered material having a frequency of inhomogeneities of less than $50 \times 10^9$ $m^{-2}$.

26. Sintered $Al_2O_3$ material comprising a mean grain size of 2.0 μm or less, and a density of no less than 98.8% of a theoretical density, a Vickers hardness greater than or equal to 1,750 at a test load from 10 to 100 N, and a flexural strength of 800 MPa or greater, said sintered material having a dimensionless defect density of less than $30 \times 10^{-3}$.

27. The sintered material of claim 26, wherein the dimensionless defect density is $10 \times 10^{-3}$.

28. The sintered material of claim 26, wherein the dimensionless defect density is $4 \times 10^{-3}$.

29. The sintered material of claim 26, wherein the dimensionless defect density is $0.6 \times 10^{-3}$.

30. The method of claim 1, wherein said two different dispersing methods are applied in series.

31. The method of claim 1, wherein said two different dispersing methods are applied simultaneously.

32. The method of claim 1, wherein said particle size has a distribution of $d_{16} > 0.065$ μm, $d_{50} \leq 0.30$ μm, $d_{84} < 0.45$ μm.

33. The method of claim 1, wherein said aqueous solution comprises dispersants selected from the group consisting of mineral acids, carboxylic acids and polycarboxylic acids.

34. The method of claim 1, wherein said mixture is supplemented with compounds containing one or more elements selected from the group consisting of Li, Mg, Ba, Sr, Zn, Fe, Co, Ni, Cr, Zr, Ti, Si, Y, Ce, La, and Y.

35. The method of claim 1, wherein said treating step comprises pressure filtration in a pressure range of 0.3 to 20.0 MPa.

36. The method of claim 1, wherein, after said treating step and prior to said heating, said unsintered body is subjected to cold isostatic pressing.

37. The method of claim 7, wherein said two different dispersing methods are applied in series.

38. The method of claim 7, wherein said two different dispersing methods are applied simultaneously.

39. A method, comprising the steps of:
   a) dispersing α-$Al_2O_3$ powder having a mean particle size $d_{50}$ of $\leq 0.30$ μm and a chemical purity of $\geq 99.9\%$ α-$Al_2O_3$, a polymerizable monomer, and a polymerization initiator in an aqueous solution to create a mixture, wherein said mixture has a solids content of α-$Al_2O_3$ powder of greater than 60% by mass, said mixture effected through the application of at least two different dispersing methods;
   b) treating said mixture by degassing said mixture under a reduced pressure of 100–300 mbar, and initiating polymerization of said polymerizable monomer through the addition of a catalyst or increasing the temperature to 55–80 degrees Celsius so as to create an unsintered body having a relative density of $p \geq 55\%$;
   c) heating said unsintered body; and
   d) sintering said unsintered body so as to create a sintered material.

40. The method of claim 39, wherein said monomer comprises acrylamide.

41. The method of claim 39, wherein said two different dispersing methods are applied in series.

42. The method of claim 39, wherein said two different dispersing methods are applied simultaneously.

43. The method of claim 39 wherein said particle size has a distribution of $d_{16} > 0.065$ μm, $d_{50} \leq 0.30$ μm, $d_{84} < 0.45$ μm.

44. The method of claim 39, wherein said treating of said unsintered body comprises pressure filtration in a pressure range of 0.3 to 20.0 MPa.

45. A method, comprising the steps of:
   a) dispersing α-$Al_2O_3$ powder having a mean particle size $d_{50}$ of $\leq 0.30$ μm and a chemical purity of $\geq 99.9\%$ α-$Al_2O_3$ in an aqueous solution to create a mixture, said dispersing of said α-$Al_2O_3$ powder effected through the application of at least two different dispersing methods;
   b) treating said mixture so as to create a shaped unsintered green intermediate product having a relative density of $p \geq 55\%$;
   c) heating said unsintered green intermediate product so as to create an unsintered precursor;
   d) crushing said unsintered precursor; and
   e) sintering said crushed unsintered precursor so as to create a sintered material.

46. The method of claim 45, wherein said dispersing methods are selected from the group consisting of stirring, milling, and ultrasound.

47. The method of claim 45, wherein said two different dispersing methods are applied in series.

48. The method of claim 45, wherein said two different dispersing methods are applied simultaneously.

49. The method of claim 45, wherein said particle size has a distribution of $d_{16} > 0.065$ μm, $d_{50} \leq 0.30$ μm, $d_{84} < 0.45$ μm.

50. The method of claim 45, wherein said aqueous solution comprises dispersants selected from the group consisting of mineral acids, carboxylic acids and polycarboxylic acids.

51. The method of claim 45, wherein said mixture is supplemented with compounds containing one or more elements selected from the group consisting of Li, Mg, Ba, Sr, Zn, Fe, Co, Ni, Cr, Zr, Ti, Si, Y, Ce, La, and Y.

52. A method, comprising the steps of:
   a) dispersing α-$Al_2O_3$ powder having a mean particle size $d_{50}$ of $\leq 0.30$ μm and a chemical purity of $\geq 99.9\%$ α-$Al_2O_3$ in an aqueous solution to create a mixture, said mixture effected through the application of at least two different dispersing methods;
   b) treating said mixture with a pressure process so as to create an unsintered precursor having a relative density of $p \geq 55\%$;
   c) heating said unsintered precursor; and
   d) sintering said unsintered precursor so as to create a sintered material.

53. The method of claim 52, wherein the pressure process is selected from the group consisting of pressure filtration, cold isostatic pressing, extrusion, and injection molding.

* * * * *

UNITED STATES PATENT AND TRADEMARK OFFICE
CERTIFICATE OF CORRECTION

PATENT NO. : 6,066,584
DATED : 05/23/2000
INVENTOR(S) : KRELL et al.

It is certified that error appears in the above-identified patent and that said Letters Patent is hereby corrected as shown below:

On column 1, after line 4, please insert --This application is a 371 of international application number PCT/EP95/01474 filed April 19, 1995.--.

On column 7, line 64, please delete "≥ 98.4%" and insert --≥98.5%--.

On column 11, line 11, please delete "2510 ± 192" and insert --2510 ± 182--.

Signed and Sealed this

Twenty-fourth Day of April, 2001

Attest:

NICHOLAS P. GODICI

Attesting Officer

Acting Director of the United States Patent and Trademark Office

Disclaimer

6,066,584 - Andreas Krell; Paul Blank, both of Dresden, Germany. SINTERED $AL_2O_3$ MATERIAL, PROCESS FOR ITS PRODUCTION AND USE OF THE MATERIAL. Patent dated May 23, 2000. Disclaimer filed September 18, 2015, by the assignee CeraMedic LLC.

I hereby disclaim the following complete claims 6, 18, 22, 24, 25, and 39-51 in said patent.

*(Official Gazette, May 24, 2022)*

(12) INTER PARTES REVIEW CERTIFICATE (314th)
United States Patent (10) Number: US 6,066,584 K1
Krell et al. (45) Certificate Issued: Feb. 5, 2018

(54) SINTERED AL2O3 MATERIAL, PROCESS FOR ITS PRODUCTION AND USE OF THE MATERIAL

(75) Inventors: Andreas Krell; Paul Blank

(73) Assignee: CERAMEDIC LLC

Trial Numbers:

IPR2015-00398 filed Dec. 12, 2014
IPR2015-00424 filed Dec. 12, 2014

Inter Partes Review Certificate for:

Patent No.: 6,066,584
Issued: May 23, 2000
Appl. No.: 08/727,409
Filed: Jan. 31, 1997

The results of IPR2015-00398 and IPR2015-00424 are reflected in this inter partes review certificate under 35 U.S.C. 318(b).

INTER PARTES REVIEW CERTIFICATE
U.S. Patent 6,066,584 K1
Trial No. IPR2015-00398
Certificate Issued Feb. 5, 2018

AS A RESULT OF THE INTER PARTES REVIEW PROCEEDING, IT HAS BEEN DETERMINED THAT:

Claims 8-10 are found patentable.

Claims 1-5, 7, 11-17, 19-21, 23, 26-38, 52 and 53 are cancelled.

\* \* \* \* \*